United States Patent [19]
Boraston

[11] Patent Number: 5,871,999
[45] Date of Patent: Feb. 16, 1999

[54] CELL CULTURE PROCESS AND MEDIUM FOR THE GROWTH OF ADHERENT ANIMAL CELLS

[75] Inventor: Robert Charles Boraston, Carshalton Beeches, United Kingdom

[73] Assignee: Alusuisse Holdings A.G., Switzerland

[21] Appl. No.: 355,103

[22] Filed: Dec. 13, 1994

Related U.S. Application Data

[63] Continuation of Ser. No. 30,419, filed as PCT/GB92/01571 filed Aug. 28, 1992, abandoned.

[30] Foreign Application Priority Data

Aug. 30, 1991 [GB] United Kingdom .................. 9118664

[51] Int. Cl.$^6$ ..................................................... C12N 5/00
[52] U.S. Cl. ................................ 435/240.25; 435/240.1; 435/240.2; 435/240.3
[58] Field of Search ............................. 435/240.1, 240.2, 435/240.25, 240.3, 325, 358, 363, 366, 383

[56] References Cited

U.S. PATENT DOCUMENTS

| | | | |
|---|---|---|---|
| 3,850,748 | 11/1974 | Cook et al. ............................... | 195/1.8 |
| 4,124,448 | 11/1978 | Narasimhan et al. ..................... | 435/68 |
| 5,122,469 | 6/1992 | Mather et al. ........................... | 435/240.2 |

FOREIGN PATENT DOCUMENTS

| | | | |
|---|---|---|---|
| 0343685 | 11/1989 | European Pat. Off. ........... | 435/240.25 |
| 0 481 791 | 4/1992 | European Pat. Off. . | |
| 0852052 | 10/1960 | United Kingdom .............. | 435/240.25 |
| 8700195 | 1/1987 | WIPO ................................ | 435/240.25 |

OTHER PUBLICATIONS

Brown et al, "On–Line Removal Of Cells From Continuous Suspension Cultures", pp. 416–420, (1991).
Goetghebeur et al, "Microsphere–Induced Aggregate Culture Of Animal Cells", pp. 423–428.
Litwin, "The Growth of Cho And BHK Cells As Suspended Agregates In Serum–Free Medium", pp. 429–433.
Ham et al, "Media And Growth Requirements", *Methods In Enzymology*, vol. 58:44–93, (1979).
Field et al, "Production Of A Chimeric Antibody For Tumour Imaging And Therapy From Chinese Hamster Ovary (CHO) And Myeloma Cells", pp. 742–744.

*Primary Examiner*—John W. Rollins
*Assistant Examiner*—Deborah K. Ware
*Attorney, Agent, or Firm*—Foley & Lardner

[57] ABSTRACT

Adherent animal cells are grown in suspension in a nutrient medium in which the molar ratio of total inorganic ions and total amino acids is reduced when compared with the corresponding ratio in known nutrient media, and is maintained at a level at which little or no cell aggregation occurs. Further, the nutrient medium contains 10:1 to about 1:1 molar ratio of total inorganic ions to total amino acids. In one further embodiment, the nutrient medium contains a total sodium ion concentration in the range of 75 to 120 mM (millimole), a total chloride ion concentration in the range of 50 to 90 mM and a total amino acid content of 20 to 50 mM. The adherent animal cells include mammalian cells such as cells belonging to a human, rat, mouse or hamster. Chinese Hamster Ovary Cells (CHO cells) are cultured using the process of the disclosed invention.

11 Claims, 12 Drawing Sheets

Growth profile in DMEM-based CHO suspension medium

Growth profile in low-salt CHO suspension medium

Distribution of aggregate size in DMEM-based CHO medium; analysis by microscopy

Distribution of aggregate size in low-salt CHO suspension medium; analysis by microscopy

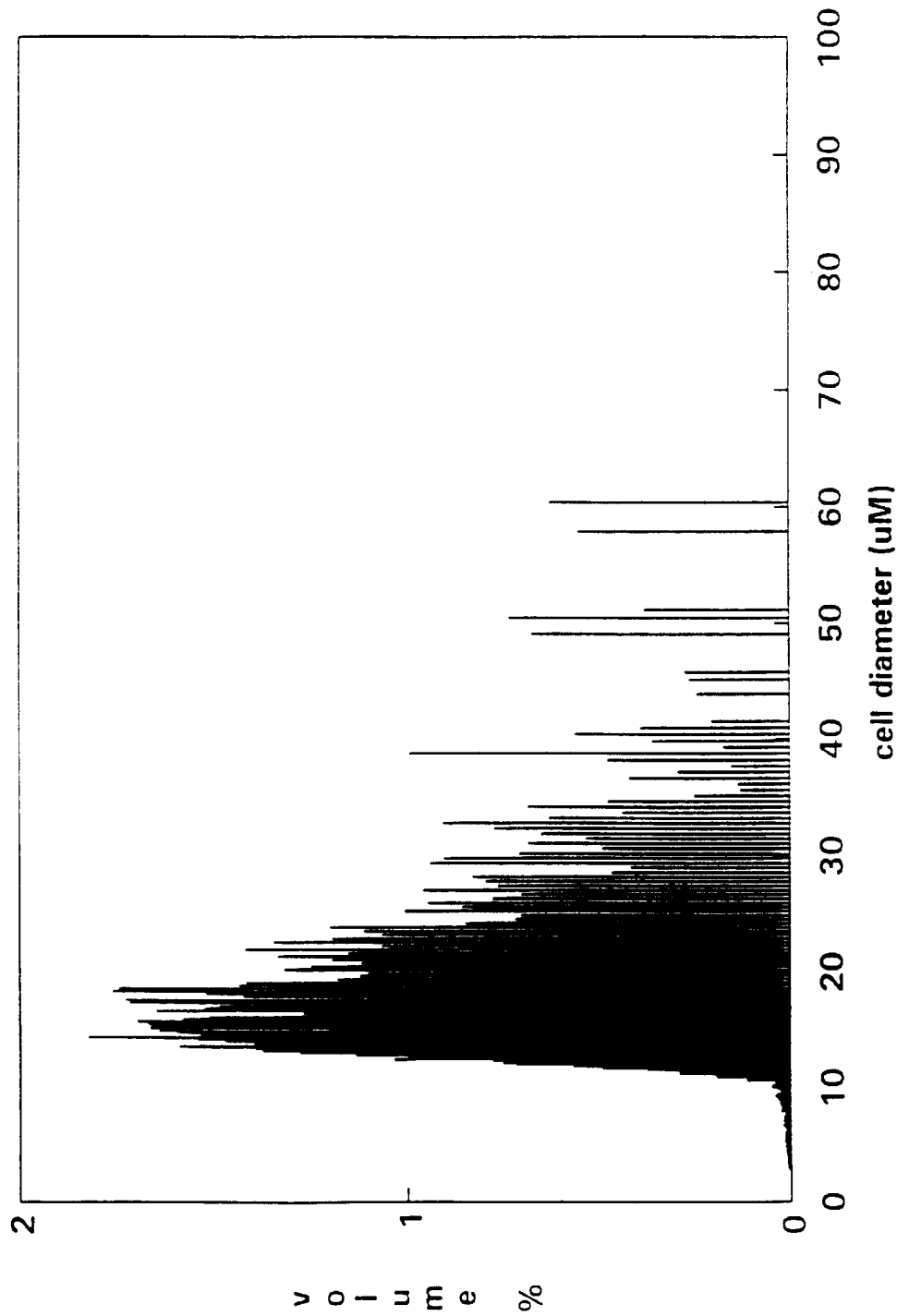

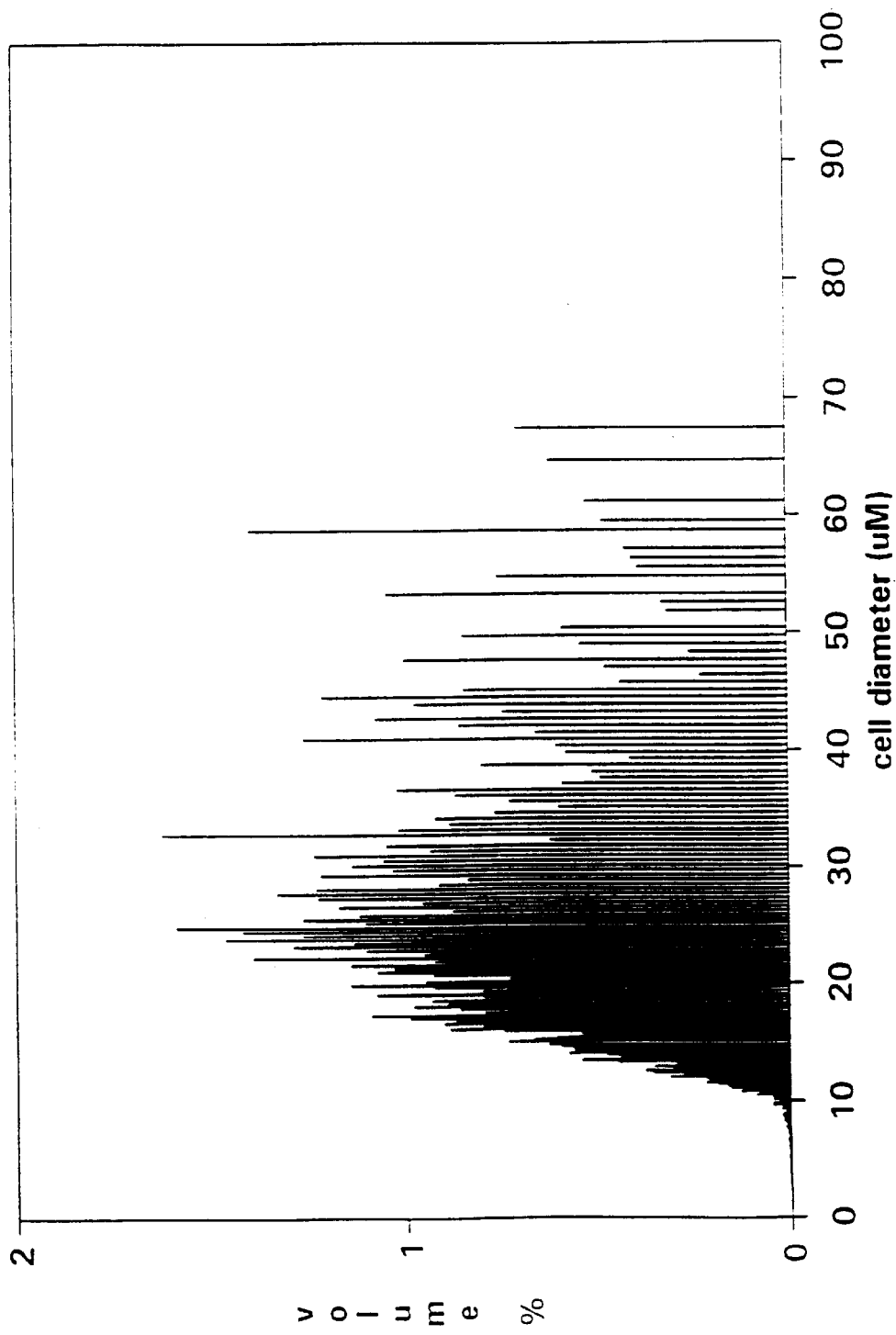

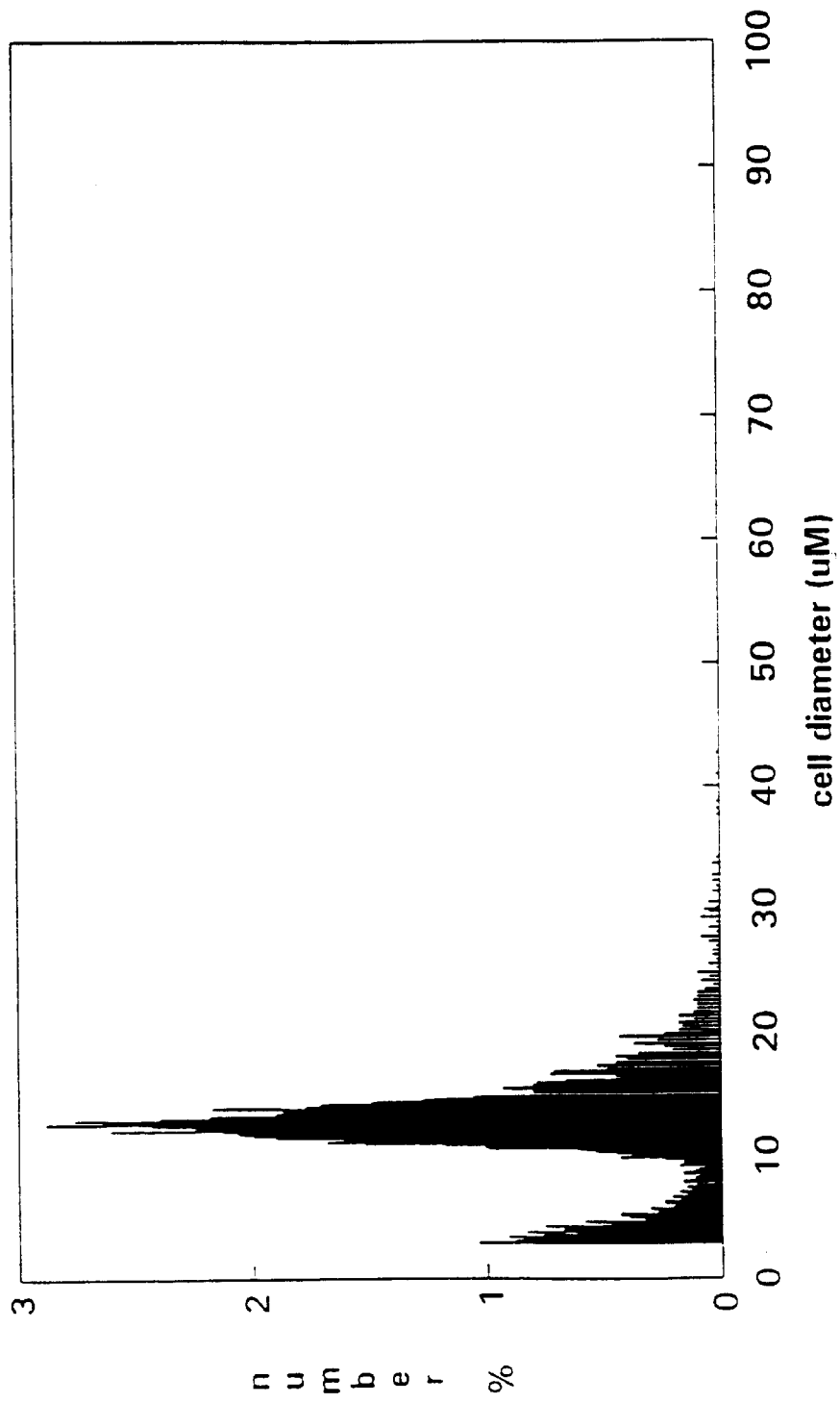

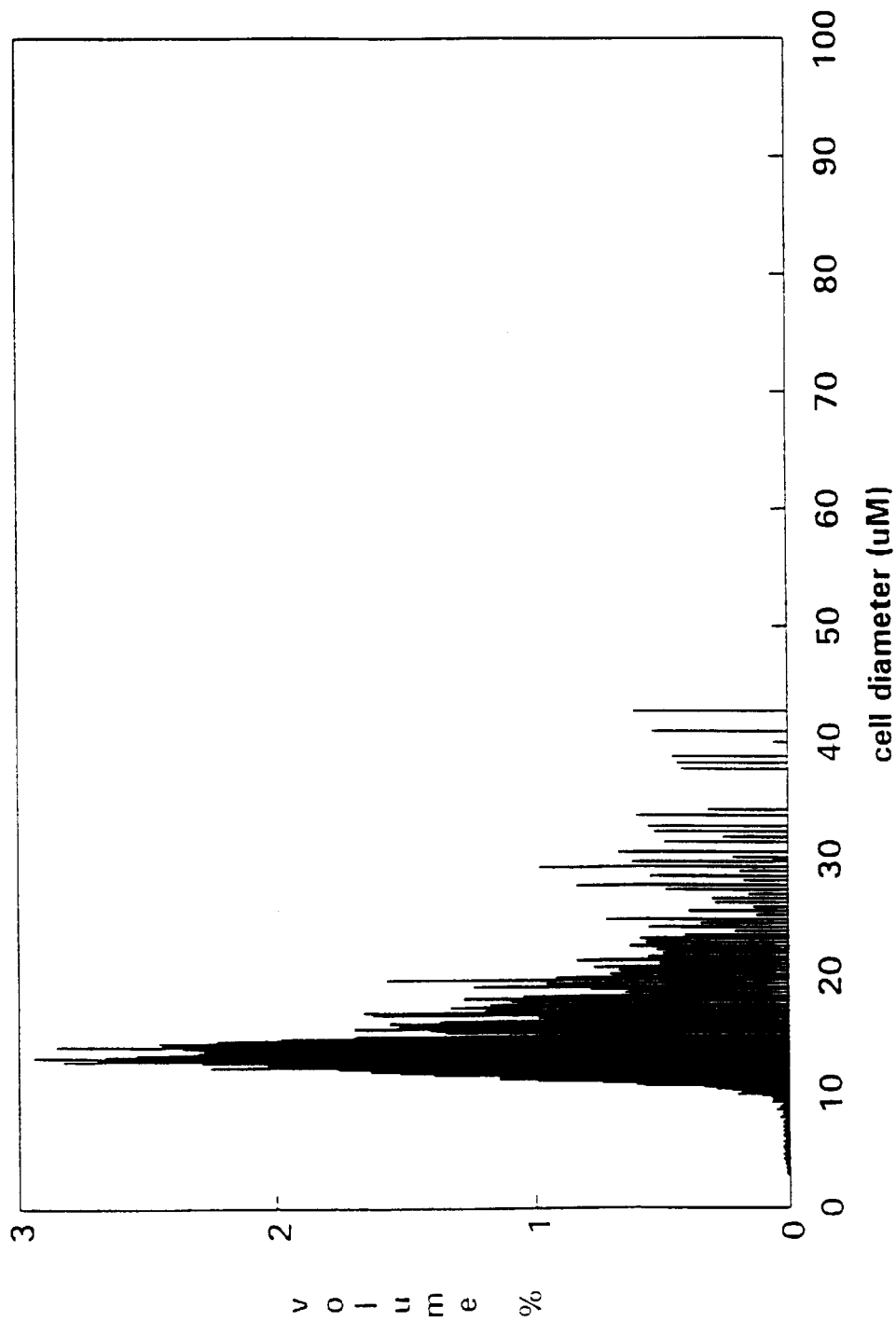

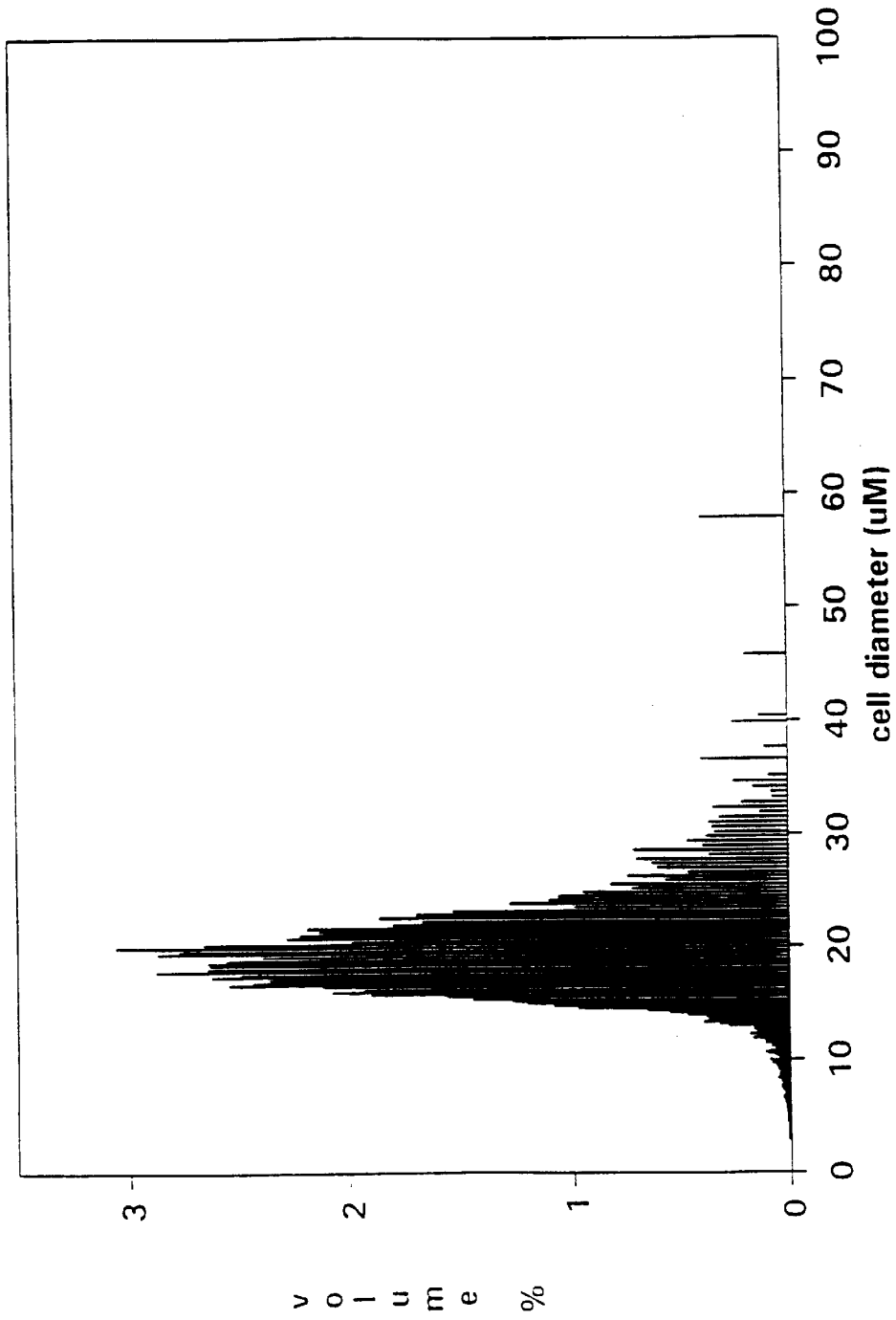

CELL CULTURE PROCESS AND MEDIUM FOR THE GROWTH OF ADHERENT ANIMAL CELLS

This application is a continuation of application Ser. No. 08/030,419, filed April 6, 1993, now abandoned (which is a national phase of PCT/GB92/01571 filed on August 28, 1992).

FIELD OF THE INVENTION

This invention relates to improvements in animal cell culture, particularly to improvements in methods for growing animal cells and nutrient media therefor.

BACKGROUND TO THE INVENTION

The use of animal cell culture for the mass production of cell products such as immunoglobulins, hormones, enzymes and other useful biologically active substances is becoming increasingly important from a commercial point of view, and currently there is considerable effort devoted to the development of cell culture techniques for the optimisation of the large scale production of these materials.

The general method of choice for the large scale culture of animal cells currently employs growth of the cells suspended in an agitated nutrient medium. The medium selected for cell growth may be expected to vary depending on the cell type, but in general will include a basal nutrient mixture of salts, sugars, amino acids and vitamins. The basal mixture can be supplemented with a biological fluid or extract, for example serum, in the absence of which most cells lose viability or fail to proliferate. Alternatively, supplement-free media may be used which generally contain a complex mixture of amino acids, salts, vitamins, trace elements, carbohydrates and other growth supporting components such as insulin, glutamine, transferrin and ethanolamine. When cultured in such media, animal cells remain viable for a finite period of time, until one or more essential nutrients in the medium become exhausted. At such time the medium may be supplemented with a feed containing one or more energy sources and one or more amino acids (see for example International Patent Specification No. WO87/00195). In this way the culture may be prolonged to increase yield of cells or cell products.

Chinese Hamster Ovary (CHO) cells are widely used in large scale culture. These cells have conventionally been grown as attached cultures, but they will also grow in suspension, a property which has allowed for relatively simple scale up in stirred tank and airlift bioreactors. Unfortunately, some CHO-derived lines which have been adapted to suspension growth can form large, tightly bound aggregates in culture. Cultivation of cells as aggregates has been described for CHO and other cell lines and indeed has been used to advantage in some cell recycle reactors which rely on cell sedimentation [see, for example, Brown, P. C. et al (1991) in Production of Biologicals from Animal Cells in Culture, R. E. Spier, J. B. Griffiths & Megnier (eds.), Butterworth Heinemann, Oxford, U.K., pp416–420, Goetghrlrud, S.E. & Wei-Shou Hu ibid, pp423–427 and Litwin, J. ibid, pp429–433]. However for batch suspension cultures cell aggregation hinders accurate cell counting, monitoring and control of the cellular environment, and may even impair transport of nutrients to, and products from, the cells.

One approach which has been suggested for solving the problem of cell aggregation in culture utilises a medium in which the calcium ion concentration has been reduced, (see European Patent Specification No. 343635). However this is not particularly satisfactory since calcium ions are required for cellular functions other than cell adhesion, and cell growth and viability may therefore be adversely affected.

SUMMARY OF THE INVENTION

We have now found that it is possible to eliminate cell aggregation in the culture of CHO-derived cell lines by controlling the molar ratio of total inorganic ions and total amino acids present in the medium. We have used this to develop a general means for the suspension culture of adherent animal cells, which is easy to operate and advantageously avoids the need to use media containing low calcium ion concentrations.

Thus according to one aspect of the invention we provide a process for the culture of adherent animal cells, wherein the adherent animal cells are cultured in suspension in a nutrient medium contained in a culture vessel, characterised in that the molar ratio of total inorganic ions and total amino acids in the nutrient medium is maintained at a level at which little or no cell aggregation occurs.

DETAILED DESCRIPTION OF THE INVENTION

In the process according to the invention, the molar ratio of total inorganic ions and total amino acids in the nutrient medium is generally that at which during the course of the culture either no cell aggregation occurs and all cells are present as single cells, or some cell aggregation occurs and cells are present as clumps containing ten or less cells.

It will be appreciated that the exact molar ratio of total inorganic ions and amino acids to be used according to the process of the invention may be varied according to the cell-line in use and the other medium components present. In general, however, the molar ratio of inorganic ions to amino acids will be substantially reduced when compared with the corresponding ratio in known media. Thus, for example, whereas the ratio in known media may range from around 15 to 1 to around 40 to 1 [see for example the media listed in Table 1 hereinafter and R. G. Ham and W. L. McKeehan in Methods in Enzymology (1979) LVIII, pp44–93] in the process according to the invention the ratio may be reduced to within the range from around 10 to 1 to around 1 to 1, especially from around 5 to 1 to around 1 to 1, for example from 4.5 to 1 to 2 to 1.

The term molar ratio of total inorganic ions and total amino acids as used herein is intended to mean the ratio of the number of moles of inorganic ions in a given volume to the number of moles of amino acids in the same volume. By inorganic ions is meant those bulk inorganic ions generally added to culture media and includes for example calcium, magnesium, potassium, sodium, chloride, nitrate, phosphate and sulphate ions. Other trace inorganic ions, for example iron, zinc and selenium ions, generally added to culture media, are usually used at much lower molarities than bulk ions and at these concentrations in the context of the present invention will have little or no effect on cell aggregation. The term amino acids is intended to mean those essential amino acids generally added to culture media and includes for example arginine, cysteine, cystine, glutamine, histidine, isoleucine, leucine, lysine, methionine, phenylalanine, threonine, tryptophan, tyrosine, and valine as well as those non-essential amino acids in general use for culture media, such as for example alanine, asparagine, aspartate, glutamate, glycine, proline and serine.

In general, to achieve the desired ratio of inorganic ions and amino acids in the process according to the invention the number of moles of sodium and chloride ions and amino acids are preferably adjusted, while the other bulk inorganic ions, especially calcium ions, are maintained in the quantities usually employed in culture media [see for example Table 1 hereinafter and R. G. Ham and W. L. McKeehan ibid]. Thus, in contrast to conventional cell culture processes the present process may be performed using a medium employing less moles of sodium and chloride ions and more moles of amino acids than known media used for conventional processes. Thus for example the total sodium ion concentration of the medium in the process according to the invention may be in the range 75 to 120 mM, especially 90 to 115 mM, and the total chloride ion concentration may be in the range 50 to 90 mM, for example 60 to 80 mM, while the total amino acid concentration may be in the range 20 to 50 mM. It will be appreciated that the exact sodium, chloride and amino acid molarity may be selected within the above ranges to suit the cell line in use, providing that the above-mentioned ratios of total inorganic ions and total amino acids are adhered to.

Media for use in the process according to the invention are new and form a further aspect of the invention. Thus according to a further aspect of the invention we provide a nutrient medium for use in the suspension culture of adherent animal cells and comprising assimilable sources of carbon, nitrogen, amino acids, inorganic ions, trace elements and optionally lipids and growth promoters or regulators, in admixture, characterised in that the molar ratio of total inorganic ions and total amino acids present in the medium is in the range from around 10 to 1 to around 1 to 1.

In a preferred medium according to the invention the molar ratio of total inorganic ions and total amino acids may be in the range from around 5 to 1 to around 1 to 1, especially in the range 4.5 to 1 to 2 to 1.

In media according to the invention, the total sodium and chloride ion concentrations, as well as the amino acid concentrations, may preferably be those discussed above in relation to the process of the invention.

In general, the medium may be any known basal medium or variants thereof, supplemented with a biological fluid or extract, or any supplement free complex medium, in which the molar ratio of total inorganic ions and total amino acids has been adjusted to be in the range from around 10 to 1 to around 1 to 1. Such media may be prepared by appropriate mixture of individual components using conventional procedures and may either be provided in liquid form, or in dry form for reconstitution before use with an appropriate buffer, e.g. a bicarbonate buffer. Suitable media for use according to the invention may be determined using preliminary small scale tests in accordance with conventional practice. Thus, for example, a suitable molar ratio of total inorganic ions and total amino acids may be determined for any cell type by observing the degree of cell aggregation, [for example by using microscopical measurements as described in the Example hereinafter], obtained by culturing the cells over a range of total inorganic ions and total amino acids concentrations.

The process and media according to the invention may be used for the culture of any adherent animal cells. The cells may be for example naturally occurring cells, genetically engineered cells, lymphoid cells, e.g. myeloma cells or hybridoma or other fused cells. Mammalian cells are particularly preferred. Particular cell types include cells of human, rat, mouse or hamster origin.

The process and media according to the invention are particularly suitable for use with Chinese Hamster Ovary cells [hereinafter referred to as CHO cells], including CHO-derived recombinant cell-lines. The process and media according to the invention may be used to culture adherent animal cells to obtain an animal cell product. Thus according to a further aspect of the invention we provide a process for obtaining an animal cell product by cell culture which comprises the steps of (1) culturing adherent animal cells which produce said product in suspension in a nutrient medium contained in a culture vessel (2) continuing the culture until said product accumulates and (3) recovering said product, characterised in that the molar ratio of total inorganic ions and total amino acids in the nutrient medium is maintained at a level at which little or no cell aggregation occurs.

Cell products which may be obtained according to the invention include any products which are produced by cultured animal cells. Typical products include polypeptides and proteins, for example immunoglobulins such as monoclonal and recombinant antibodies and fragments thereof, hormones such as erythropoietin and growth hormone, e.g. human growth hormone, lymphokines such as interferon, interleukins such as interleukin 1 and interleukin 2, industrially and therapeutically useful enzymes such as tissue plasminogen activator, and enzyme inhibitors such as tissue inhibitor of metalloproteinases. In the processes according to the invention, the animal cells may generally be cultured in suspension in the nutrient medium in a suitable culture vessel, for example a stirred tank or airlift fermenter, using known culture techniques.

Thus, for example, a seed culture of suitable cells, obtained by conventional techniques, may be used to inoculate the nutrient medium. In general, the number of cells used for inoculation will be in the range $1 \times 10^5$ to $5 \times 10^5$ cells $ml^{-1}$ or less. The cells are then cultured until a desired cell density is reached and/or until sufficient product has accumulated.

If desired, one or more amino acids, energy sources and other nutrients may be added during the culture, for example as part of a concentrated feed, or separately, in accordance with conventional practice, providing of course that the molar ratio of total inorganic ions and total amino acids is maintained within the level sufficient to prevent cell aggregation.

The production of the desired products during the culture may be monitored using any appropriate assay for the particular product in question. Thus, for example, where the product is a polypeptide or protein, the production of this may be monitored by general assay techniques such as enzyme-linked immunoabsorbent assay or immunoradiometric assay adapted for use with the particular polypeptide or protein.

Where in the process according to the invention it is desired to isolate the cell product obtained, this may be achieved using conventional separation and purification technqiues. Thus, for example, where the product is secreted by the cells into the medium it may be separated from the cells using techniques such as centrifugation and filtration and then further purified using, for example, affinity purification techniques, such as affinity chromatography. Where the product is not secreted by the cells the above methods may still be used, but after the cells have first been lysed to release the product.

BRIEF DESCRIPTION OF THE DRAWINGS

The invention is now described by way of illustration only in the following Example which refers to the accompanying diagrams in which.

DESCRIPTION OF SPECIFIC EMBODIMENTS

Example

Figure 1:
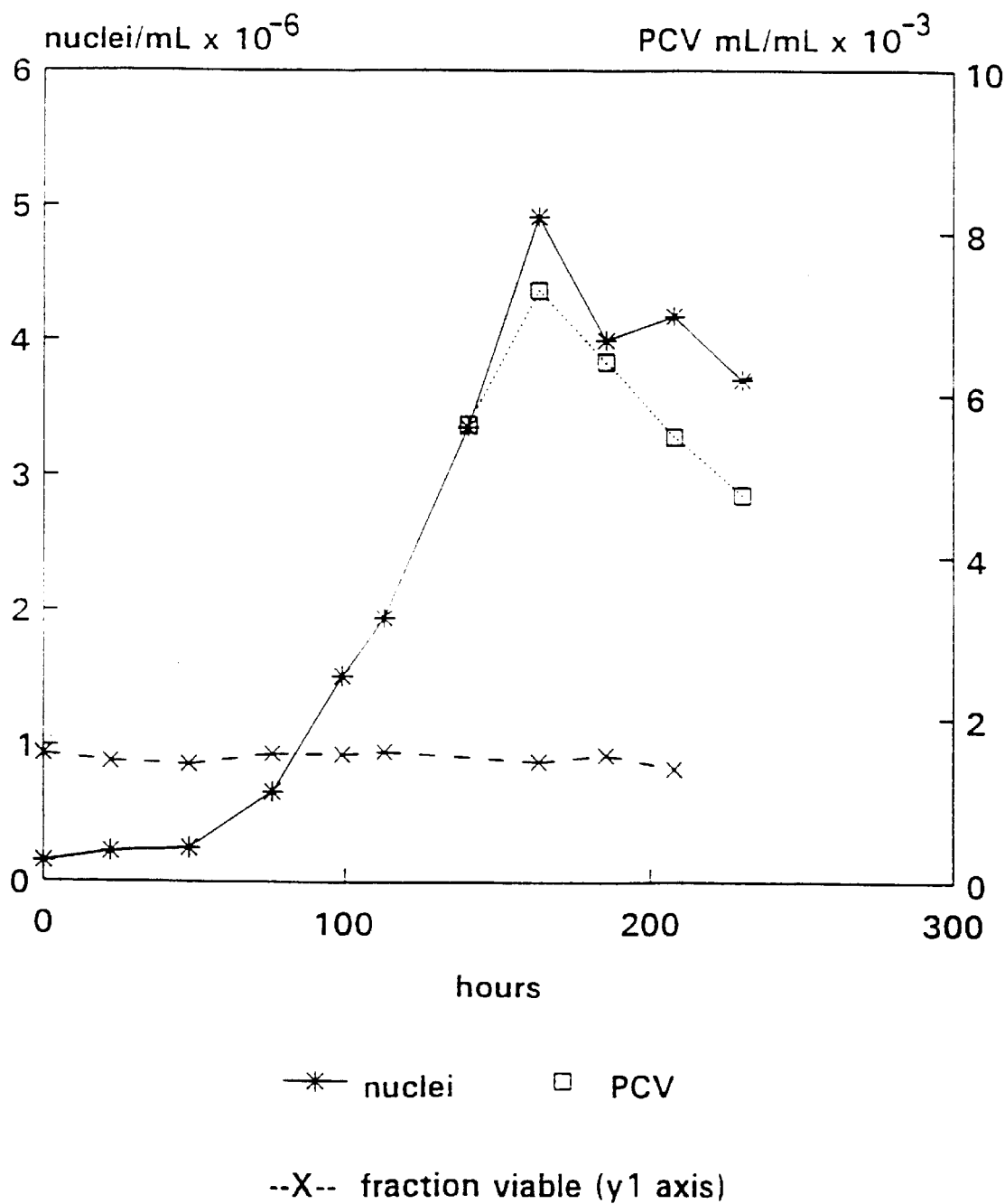
FIG. 1 is a graph showing the growth profile of the CHO-derived recombinant cell line 11G9 in a Dulbecco's Modification of Eagle's medium (DMEM) based suspension medium.

The cell line used, 11G9, was a CHO-derived recombinant line bearing a single copy of each of the genes encoding heavy and light chains of a chimeric IgG antibody [Field, R. P. et al in Production of Biologicals from Animal Cells in Culture, ibid, pp742–744]. This line has been observed to form large aggregates when cultured in conventional medium formulations.

Cultures were made in stirred bioreactors of 6L working volume. Culture temperature was maintained at 36.5° C., dissolved oxygen tension at 15–20% of air saturation by sparging nitrogen or air as a ballast gas with automatic injection of air or oxygen respectively, and pH at 7.0–7.2 by automatic injection of $CO_2$ into the sparged gas mixture or of molar NaOH into the culture. The total gas sparge rate was up to 0.15 volumes per volume per minute and the agitator tip speed was 45 cm/s.

Two base formulations were tested. The first was a Dulbecco's Modification of Eagle's medium (DMEM) derived base in which glutamic acid had been substituted for glutamine and a number of other amino acids increased in concentration to meet the particular nutritional requirements of CHO cells. The second was a similar base developed specifically for suspension growth of CEO's [hereinafter termed a CEO suspension medium] but in which the sodium and chloride ion content had been reduced, while the amino acid content had been increased when compared to conventional media (see Table 1 below in which the inorganic ion and amino acid composition of four other standard media are also given). In both instances the calcium ion content was maintained at around the level found in standard media.

TABLE 1

|  | $Na^+$ mM | $Cl^-$ mM | $Ca^{++}$ mM | total inorg ions mM [1] | total amino acids mM [2] | molar ratio [1]:[2] |
|---|---|---|---|---|---|---|
| Dulbecco's Modification of Eagle's Medium (DMEM) | 155 | 120 | 1.8 | 162 | 11 | 14.7 |
| Ham's F12 | 146 | 135 | 0.3 | 149 | 4 | 37.3 |
| MEM alpha | 145 | 126 | 1.8 | 152 | 9 | 16.9 |
| Fischer's medium | 152 | 145 | 0.6 | 158 | 5 | 31.6 |
| RPMI 1640 | 138 | 104 | 0.4 | 138 | 6 | 23.0 |
| Low salt/high amino acids suspension medium | 113 | 75 | 1.0 | 100 | 41 | 2.4 |

Estimations of biomass concentration, and of the degree of cell aggregation, were made by several methods as follows:

Cells were counted microscopically using a haemocyto meter. Exclusion of trypan blue stain was used to determine viability. In aggregates of greater than 10 cells, counting was impossible so the aggregate diameter was estimated (mean of four measurements) using a calibrated micrometer eyepiece. The volume of aggregates was calculated as $4/3 \times 3.142 \times r^3$ where r is the radius of the aggregate. Viable and total cell blue counts were also made after treating cells with trypsin to disperse aggregates into a single-cell suspension.

Nuclear counts were made microscopically after lysing cells in 0.1 M citric acid containing 0.1% (w/v) crystal violet stain. This method gave a 'total' count which was generally close to the 'total' count obtained with trypan blue following trypsin treatment.

Packed cell volume (PCV) was measured. Cells were sedimented from culture samples by centrifugation, then the cell pellet transferred to a graduated capillary tube and sedimented by centrifugation to constant volume.

From these various measurements it was possible to calculate values for mean cell volume as Mean cell volume=packed cell volume/crystal violet count and the number of cells in an aggregate of measured size was calculated as number of cells=volume of aggregate/mean cell volume Thus from these microscopical and physical measurements it was possible to build up an analysis of aggregate size distribution through the timecourse of the fermenter cultures.

Biomass concentration was also measured, together with an analysis of aggregate size distribution, using a Coulter Multisizer II (Coulter Electronics Ltd., Luton, Beds, UK).

RESULTS

Figure 2:
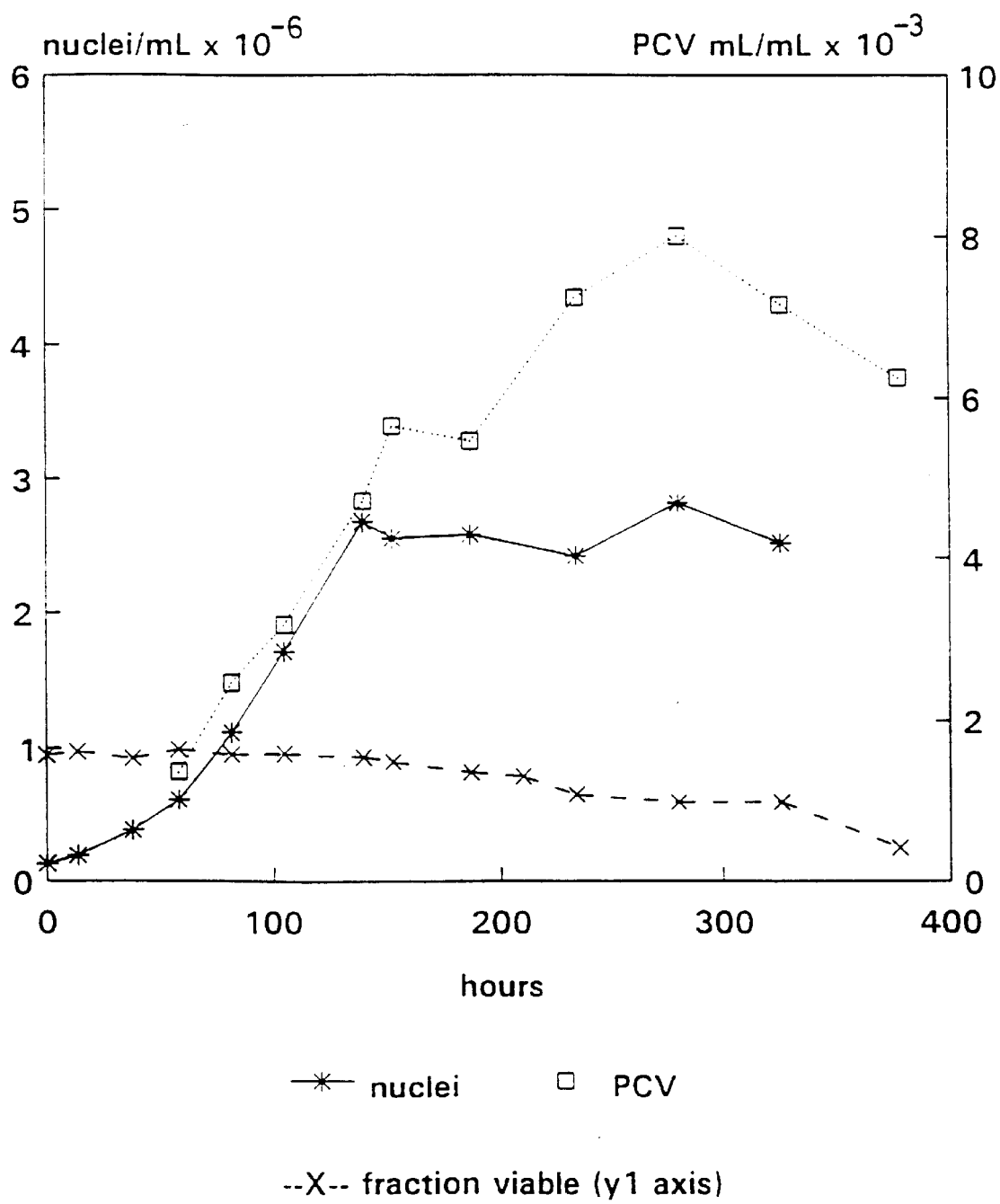
FIG. 2 is a graph showing the growth profile of the CHO-derived recombinant cell line 11G9 in a low salt, high amino acid suspension medium.

Cell growth profiles, as measured by nuclear counts and PCV, together with an estimate of viability from trypan blue counts, for the DMEM-based medium and for the CHO suspension medium are shown in FIGS. 1 and 2 respectively.

Figure 3:
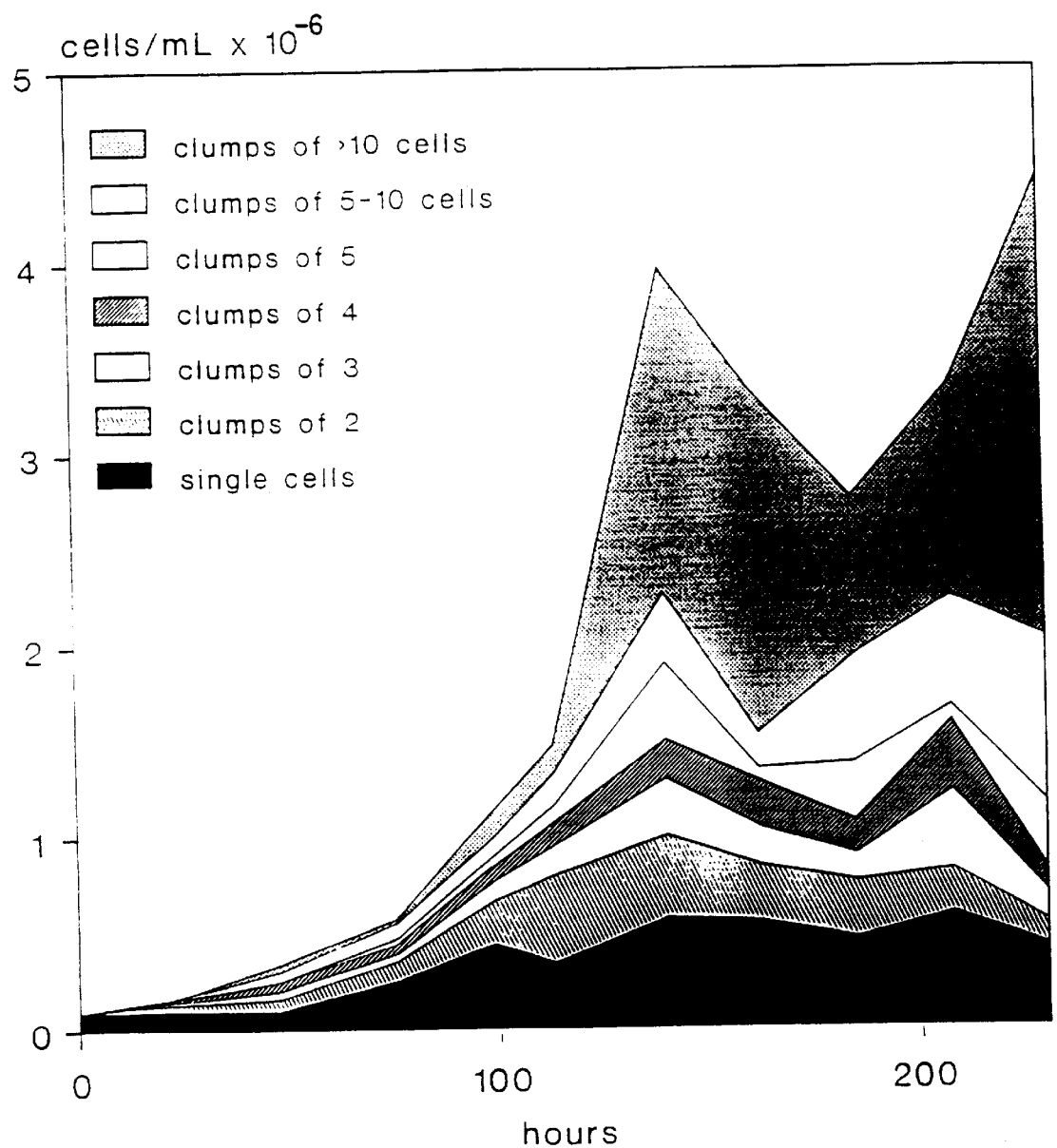
FIG. 3 illustrates the distribution of single cells and cell aggregates of different sizes during the time course of a culture of the CHO-derived recombinant cell line 11G9 in a Dulbecco's Modification of Eagle's medium (DMEM) based suspension medium.
Figure 4:
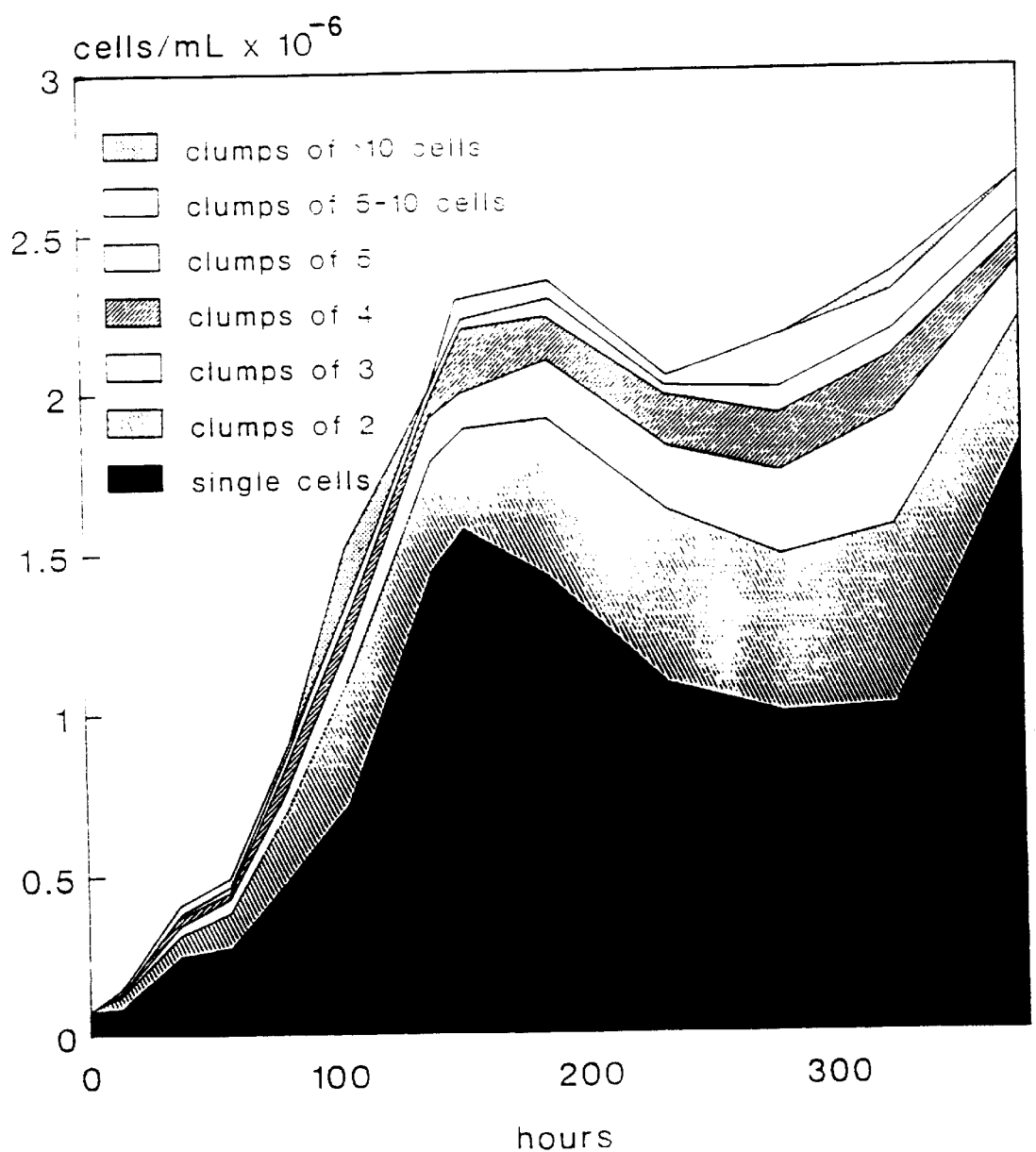
FIG. 4 illustrates the distribution of single cells and cell aggregates of different sizes during the time course of a culture of the CHO-derived recombinant cell line 11G9 in a low salt, high amino acid suspension medium.

An analysis of the degree of aggregation through the timecourse of the cultures, derived from microscopical measurments, is shown in FIGS. 3 & 4. These plots represent the growth curves obtained by trypan blue counts (direct counts for single cells and aggregates of up to 10 cells; calculated estimates of cells per aggregate for aggregates of greater than 10 cells). Each plot is divided by area to represent the distribution of the population as single cells and as aggregates of different sizes. In the DMEM-based medium aggregation was conspicuous and increased through the timecourse of the culture. Aggregates as large as 86 βM in diameter, calculated to contain up to 229 cells, were observed. By contrast, in the low salt/high amino acids CHO suspension medium, the majority of cells were either single cells or as clumps of only 2–3 cells. Rarely did aggregate size approach or exceed 10 cells.

Figure 5:
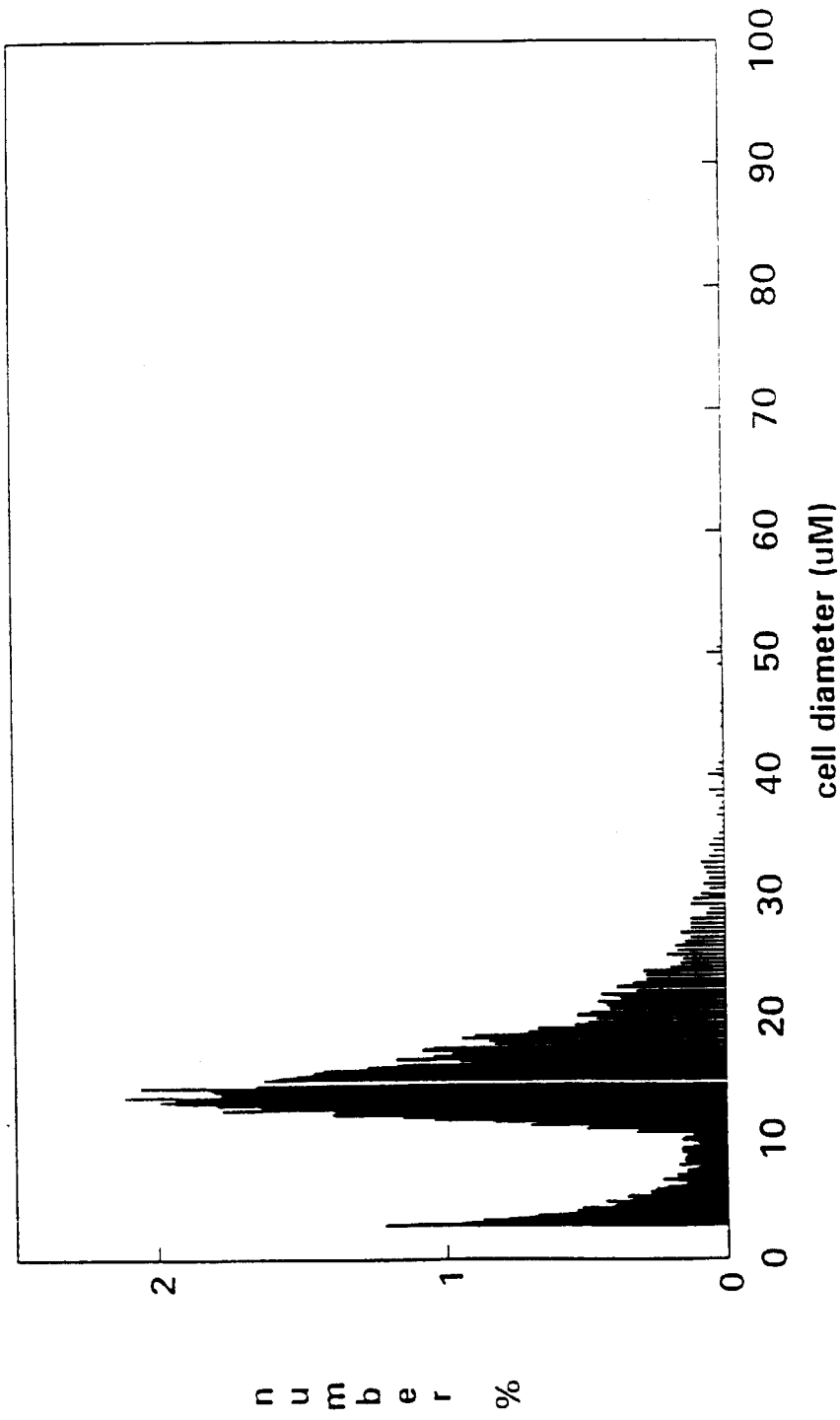
FIG. 5 illustrates the percentage frequency of cells and cell aggregates at various time points during the culture of the CHO-derived recombinant cell line 11G9 in a Dulbecco's Modification of Eagle's medium (DMEM) based suspension medium.

These observations are backed up by analyses made using the Coulter Multisizer. FIG. 5a shows the percentage frequency of cells and aggregates of different sizes for a cultre in DMEM-based medium, 99 hours after inoculation, when the cell concentration was approximately $1 \times 10^6$/mL.

Figure 5D:
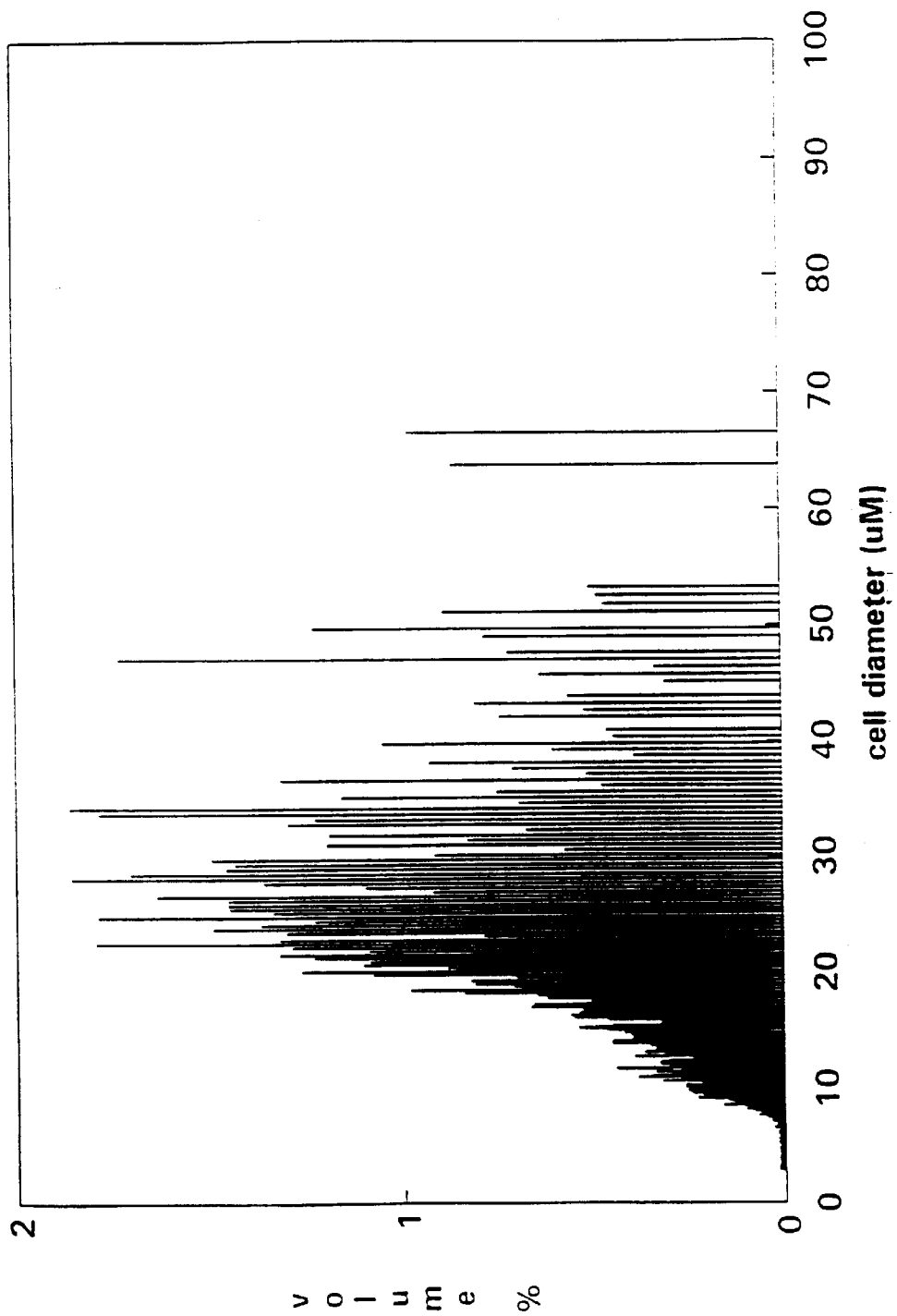
Figure 6D:
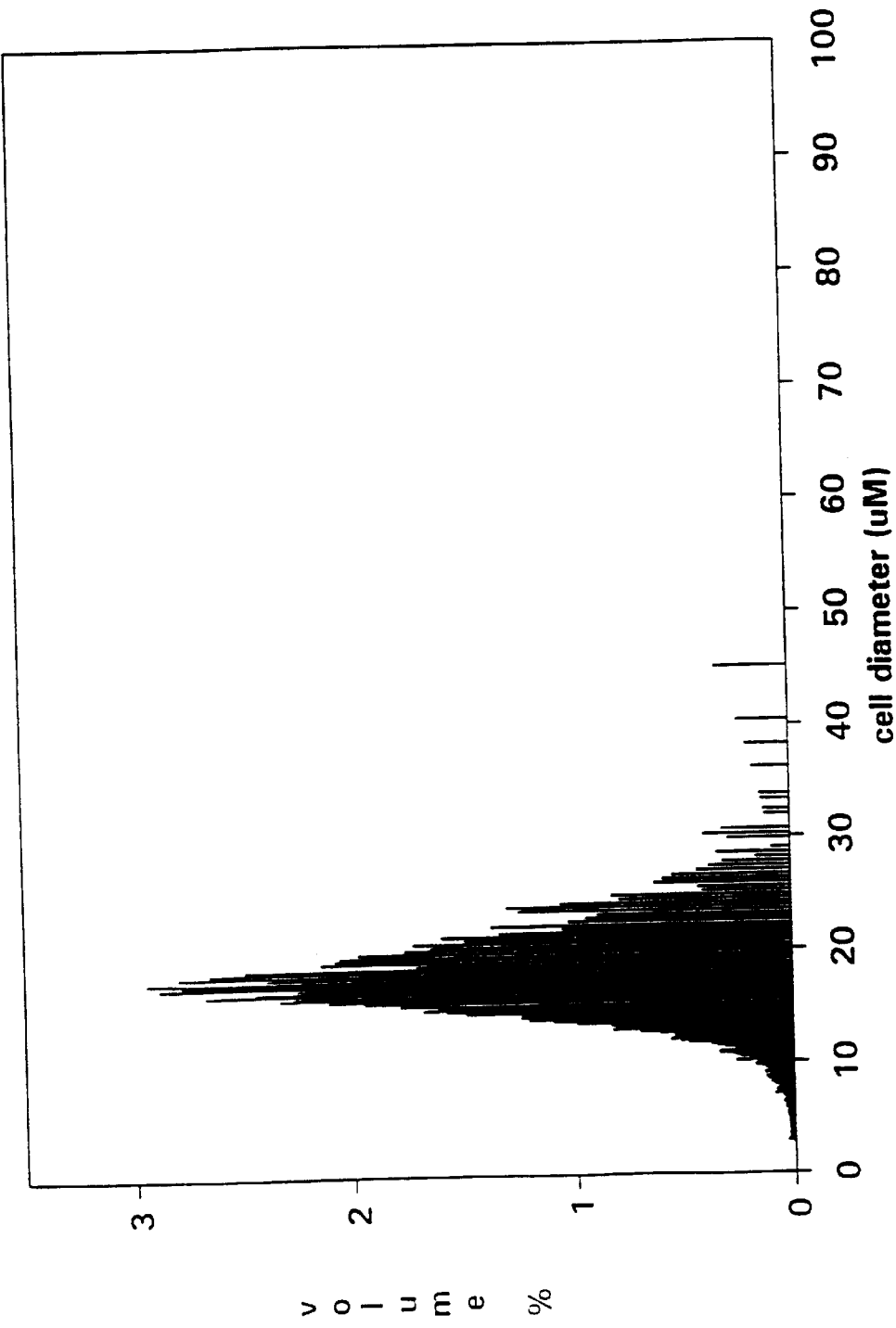
FIG. 6 illustrates the percentage frequency of cells and cell aggregates at various time points during the culture of the CHO-derived recombinant cell line 11G9 in a low salt, high amino acid suspension medium.

The majority of particles consist of single cells (diameter 13–14 uM agrees well with estimates of mean cell diameter calculated from measurements of PCV), however there is a right skew to the distribution indicating a smaller number of relatively large cell aggregates. When this distribution is represented as volume (FIG. 5b) it becomes clear that a large proportion of the total biomass is as aggregates rather than as single cells. Following the timecourse of the culture (FIGS. 5c and 5d) cell clumping increases with increasing cell concentration until the major part of the biomass occurs as large aggregates. FIG. 6 shows the timecourse of analyses for the culture grown in the low salt/high amino acids CHO suspension medium. The analysis of cell number against diameter at 85 hours shows a predominance of single cells with relatively little skew in the distribution (FIG. 6a). This is substantiated by the analysis of biovolume (FIG. 6b); most of the biomass is as single cells. In fact the aggregates present at 85 hours were probably derived from the flask-grown inoculum as, following the timecourse of analyses through FIGS. 6c & 6d, these aggregates disappear and almost all the biomass occurs as single cells.

The above experiments were repeated with a medium similar to the above low salt/high amino acids suspension medium, but in this instance the medium contained total sodium ions at 104 mM, total chloride ions at 74 mM, total calcium ions at 1.0 mM, total inorganic ions at 99 mM, total amino acids at 23 mM and an ion:amino acid ratio of 4.3. With this medium cell aggregates also disappear and as before almost all the biomass occurs as single cells.

CONCLUSIONS

In conventional media, cultured CHO-derived cell lines can spontaneously aggregate to form large cell masses as shown above with regard to the DMEM - based medium. This aggregation could be eliminated by using a low salt/high amino acids medium.

I claim:

1. A process for the culture of adherent animal cells, comprising the step of culturing the adherent animal cells in suspension in a nutrient medium contained in a culture vessel, wherein the molar ratio of total inorganic ions to total amino acids in the nutrient medium is maintained within a range from about 10:1 to about 1:1.

2. The process according to claim 1 wherein the nutrient medium comprises a total sodium ion concentration in the range of 75 to 120 mM; a total chloride ion concentration in the range of 50 to 90 mM; and a total amino acid content in the range of 20 to 50 mM.

3. The process according to claim 1 wherein the adherent animal cells are mammalian cells.

4. The process according to claim 3 wherein the mammalian cells are cells of human, rat, mouse or hamster origin.

5. The process according to claim 3 wherein the mammalian cells are Chinese Hamster Ovary Cells.

6. A nutrient medium for use in the suspension culture of adherent animal cells and comprising assimilable sources of carbon, nitrogen, amino acids, inorganic ions and trace elements, in admixture, wherein the molar ratio of total inorganic ions to total amino acids present in the medium is in the range from about 10:1 to about 1:1.

7. The nutrient medium according to claim 6 wherein the molar ratio of total inorganic ions to total amino acids is in the range from about 5:1 to about 1:1.

8. The nutrient medium according to claim 6 wherein the nutrient medium comprises a total sodium ion concentration in the range of 75 to 120 mM; a total chloride ion concentration in the range of 50 to 90 mM; and a total amino acid concentration in the range of 20 to 50 mM.

9. A process for obtaining an animal cell product by cell culture which comprises the steps of (1) culturing adherent animal cells which produce said product in suspension in a nutrient medium contained in a culture vessel (2) continuing the culture in said nutrient medium until said product accumulates and (3) recovering said product, wherein the molar ratio of total inorganic ions to total amino acids in said nutrient medium is maintained within a range from about 10:1 to about 1:1.

10. The process of claim 9, wherein said nutrient medium further comprises lipids.

11. The process of claim 9, wherein said nutrient medium further comprises growth promoters or regulators.

* * * * *